12/6/77 XR 4,062,020

United States Patent [19]

Berglund

[11] 4,062,020

[45] Dec. 6, 1977

[54] CIRCUIT ARRANGEMENT FOR THE FREQUENCY ANALYSIS OF A SIGNAL

[75] Inventor: Kurt Berglund, Solna, Sweden

[73] Assignee: Siemens Aktiengesellschaft, Berlin & Munich, Germany

[21] Appl. No.: 664,414

[22] Filed: Mar. 5, 1976

[30] Foreign Application Priority Data

Mar. 24, 1975 Germany ............................ 2512939

[51] Int. Cl.[2] ............................................ G01R 23/18

[52] U.S. Cl. .............................. 346/33 R; 324/77 C; 346/75

[58] Field of Search ......................... 346/33 R, 35, 75; 324/77 C, 77 CS, 77 E; 179/1 SP

[56] References Cited

U.S. PATENT DOCUMENTS

| | | | |
|---|---|---|---|
| 2,159,790 | 5/1939 | Freystedt | 324/77 E |
| 2,492,062 | 12/1949 | Potter | 324/77 E |
| 2,566,443 | 9/1951 | Elmquist | 346/75 |
| 3,582,957 | 6/1971 | Herleikson | 346/33 R |

*Primary Examiner*—Joseph W. Hartary
*Attorney, Agent, or Firm*—Hill, Gross, Simpson, Van Santen, Steadman, Chiara & Simpson

[57] ABSTRACT

A circuit arrangement for the frequency analysis of a signal, including a plurality of band filter channels, to whose inputs there is transmitted in parallel the signal which is to be analyzed, and which possess band filters having different limiting or boundary frequencies and containing rectifiers and integrators for the integration of the rectified output signals of the band filters at predetermined integrating intervals; and having a scanning arrangement connected to the outputs thereof which interrogates the integration results pursuant to predetermined intervals.

8 Claims, 3 Drawing Figures

CIRCUIT ARRANGEMENT FOR THE FREQUENCY ANALYSIS OF A SIGNAL

FIELD OF THE INVENTION

The present invention relates to a circuit arrangement for the frequency analysis of a signal, including a plurality of band filter channels, to whose inputs there is transmitted in parallel the signal which is to be analyzed, and which possess band filters having different limiting or boundary frequencies and containing rectifiers and integrators for the integration of the rectified output signals of the band filters at predetermined integrating intervals,; and having a scanning arrangement connected to the outputs thereof which interrogates the integration results pursuant to predetermined intervals.

DISCUSSION OF THE PRIOR ART

In a known circuit arrangement of that type, which serves in medicine for the frequency analysis of an EEG signal and which is connected to a recording installation, the result is reproduced in the form of a diagram on a recording paper, for example, a stack histogram, in which the stack lengths are proportional to the integrating results. Hereby, the integration intervals for the integrators are equally large, and namely about 10 to 20 seconds, so that there can be obtained the lower frequencies of 1 to 2 Hz. However, this has the disadvantage that momentary signals of higher frequencies are not obtained separately, but are integrated at the end of the integration intervals within the total result of the corresponding band filter channel.

SUMMARY OF THE INVENTION

Accordingly, it is an object of the present invention to provide a circuit arrangement of the above-mentioned type which can determine low frequencies, as well as momentary signals of the high frequencies of a signal, which is constituted of a frequency mixture.

The foregoing object is inventively attained in that means are provided which so determine the integration intervals for the integrator in dependence upon the median transmissive or pass frequencies of the band filters, whereby the integration intervals reduce with an increasing median transmissive frequency for the band filters, and that switching elements are connected to the outputs of the integrators for correlation of each integration result to the corresponding integration interval.

In the subject matter of the invention, the integration interval of a band filter channel is that much longer, the lower the median frequency of the band filter. Thus, on the one hand, it is sufficiently lengthy so as to afford a determination of the output signal of the band filter and, on the other hand, sufficiently short so that, at a higher median frequency, there results a selective determination of momentary signals of higher frequencies.

An advantageous further feature of the invention contemplates that the scanning installation of the circuit arrangement be so constructed that it scans the integration results at least once for each shortest integration interval, and that it is connected to a jet recorder which contains a jet transmitter directing a recording jet onto a recording carrier, means for producing a relative movement between the jet transmitter and the recording carrier in two approximately mutually perpendicularly oriented directions within the context of effecting a linewise image recording, and a modulating device for the intensity of the recorded lines, the latter of which is controlled through the output signal of the scanning installation, and means which synchronize the scanning of the integration results with the movement of the recording jet. Hereby it is attained that on the littlest possible recording paper there is recorded the greatest possible amount of information. For example, the longest integration interval can be 16 seconds and the shortest 1 second. The spacing between the sequentially following lines can be 0.2 mm for an ink jet recorder without resultant loss of the resolution. The normal paper speed in an EEG recorder is 30 mm per second. A recording which requires a 30 mm paper recording length in the state of the art, in this embodiment of the invention can thus be applied on a 0.2 mm paper length, in effect, a reduction of about 150 : 1.

BRIEF DESCRIPTION OF THE DRAWINGS

Further advantages and details of the invention may now be ascertained from the following exemplary embodiments, taken in conjunction with the accompanying drawings; in which.

DETAILED DESCRIPTION

Figure 1:
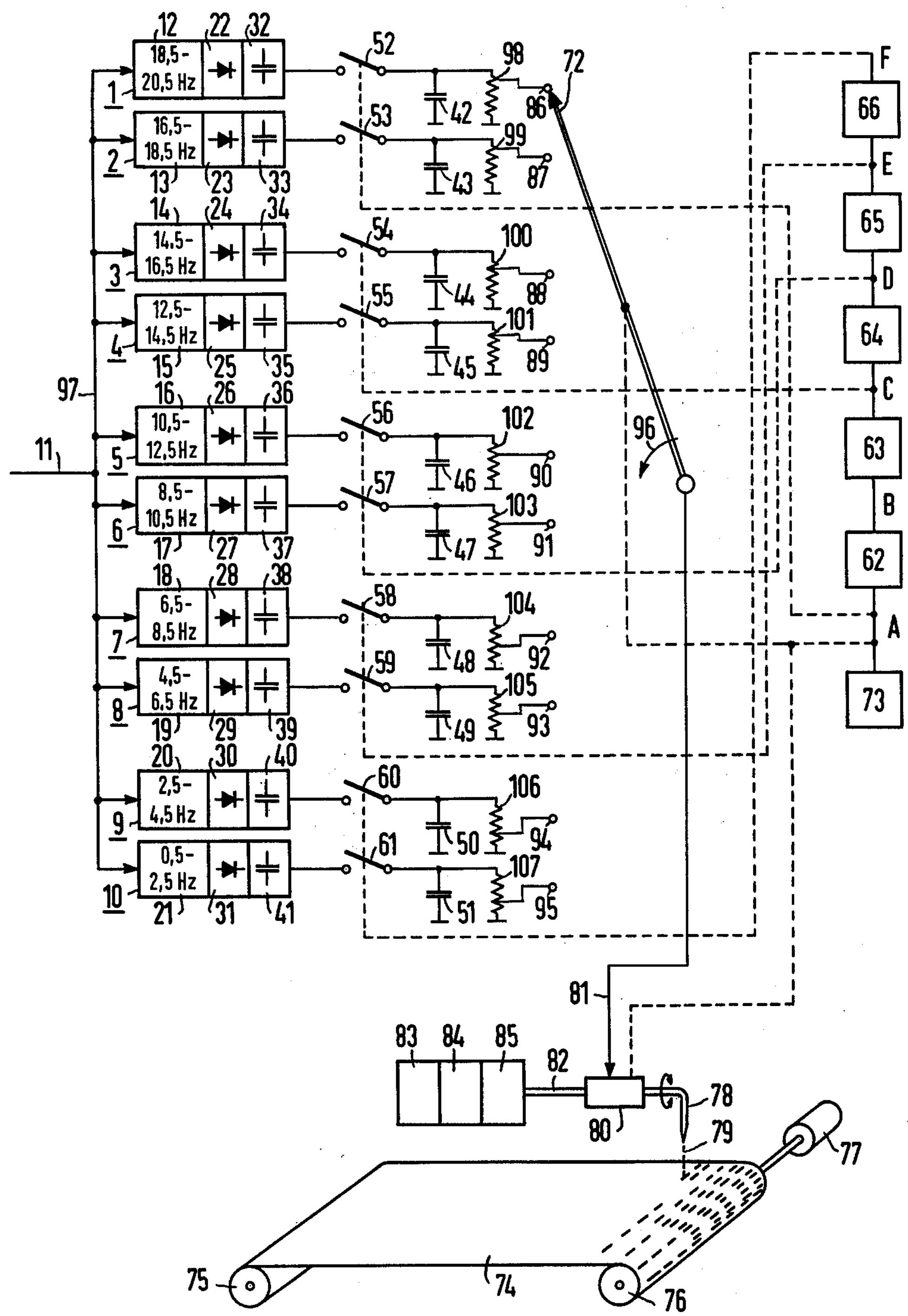
FIG. 1 is a schematic representation of an inventive circuit arrangement employed in conjuction with a recording installation.

Illustrated in FIG. 1 is a circuit arrangement for the frequency analysis of a signal, for example, an EEG signal. The circuit arrangement possesses a number of band filter channels 1 through 10. The band filters 12 through 21 of the channels 1 through 10 have different limiting frequencies whose values may be ascertained from FIG. 1. Additionally, connected to the band filters 12 through 21 are rectifiers 22 through 31 and integrators 32 through 41. Arranged at the outputs of the band filter channels 1 through 10 are signal storages 42 through 51 which are in the form of condensers, and located between these signal storages and the integrators 32 through 41 are switch elements 52 through 61.

Provided for the control of the switch elements 52 through 61 are impulse generators 62 through 66, 73, which form a frequency reducer chain or sequence, and whose output signals presently concurrently actuate two switch elements. Thus, the switch elements 52, 53 are controlled by the impulse generator 73, the switch elements 54, 55 by the impulse generator 63, the elements 56, 57 by the generator 64, the elements 58, 59 by the generator 65, and the switch elements 60, 61 by the impulse generator 66. Finally, each of the band filter channels 1 through 10 has a voltage divider 98 through 107 associated therewith.

Connected to the outputs of the band filter channels is a scanning installation 72 which, in a stepwise manner, synchronously scans the channel outputs 86 through 95, through the output signal of the impulse generator 73. The impulse generator additionally delivers the input impulse sequence for the frequency reducer chain 62 through 66.

The scanning installation 72 is additionally connected to a jet recorder. This jet recorder consists of a recording carrier 74 which is conveyed from a roller 75 onto a roller 76, and the latter of which is driven by means of an electromotor 77. An image is recorded across the width of the recording carrier 74 which, for instance, may be a paper web, and which is produced by a recording nozzle 78 directing a fine jet 79 of a recording liquid onto the recording carrier 74. The nozzle 78 is movable perpendicular to the direction of movement of the recording carrier 74 through the intermediary of an adjusting arrangement 80 (modulation arrangement), which is controlled by means of a voltage applied to the input 81. The movement of the adjusting arrangement 80 is synchronized through the impulse generator 73 with the scanning of the band filter channels 1 through 10. The nozzle 78 obtains ink through a conduit 82 from an ink supply receptacle 83. Located intermediate the conduit 82 and the supply receptacle 83 is an ink supply pump 84, and pressure regulator 85 which provides for a constant ink pressure in the conduit 82, and thereby for a uniform liquid jet 79.

Figure 2:
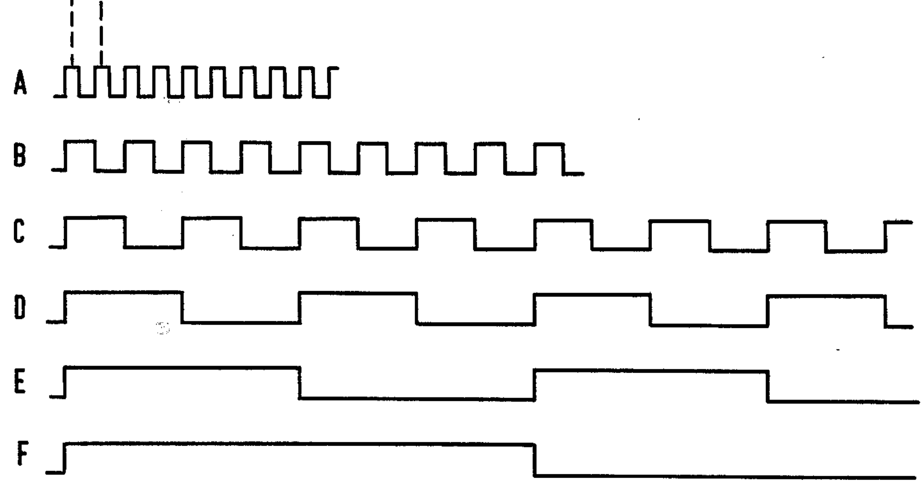
FIG. 2 is a graphical representation of impulse sequences for determining the integration intervals in the recording arrangement pursuant to FIG. 1.

Upon considering FIG. 2 in conjunction with FIG. 1, there is ascertained that the integrating interval of a band filter channel is that much longer, the lower the median frequency of the band filter. At a lower median frequency the interval is thus sufficiently lengthy so as to afford a determination of the output signal of the band filter. However, on the other hand, at a higher median frequency there is also afforded a selective determination of momentary output signals (rapid frequency change) of the band filters due to the shorter integrating interval.

Through intermediary of the liquid jet 79, an image (FIG. 3) is recorded in a linewise manner on the recording carrier 74. For example, this recording may be effected with a continuous conveyance of the recording carrier 74. An intensity modulation of the recorded lines is effectuated in that the speed is varied at which the liquid jet 79 is moved perpendicular to the direction of movement of the recording carrier 74. When this speed is high, then the intensity of the recorded lines is low, and when it is low then the intensity is high. It is also possible that the liquid jet be moved so rapidly in relation to the recording carrier, that the recording does no longer occur. Furthermore, it is possible that the speed at which the liquid jet is moved may be lowered so far that, at a further reduction, no intensity increase (for instance, darkening) is any longer possible.

The signal which is to be analyzed is conducted through the conduit 11 in parallel with the inputs 97 of the band filter channels 1 through 10. The signal which is passed through by the present band filter is rectified and integrated in that particular channel.

The switch elements 52 through 61 are actuated through the generated impulse sequences A and C through F (FIG. 2) of the synchronously operating impulse generators 62 through 66. The impulse sequence B controls no switch element; the impulse generator 62 serves for the reducing coupling of the chain 63 through 66 to the impulse generator 73. The switch elements 52, 53 are thereby controlled through the impulse sequence A, the switch elements 54, 55 through the impulse sequence C, the switch elements 56, 57 through the impulse sequence D, the switch elements 58, 59 through the impulse sequence E, and the switch elements 60, 61 through the impulse sequence F; meaning, the duration during which the switch elements are closed is dependent upon the present impulse length and is reversely proportional to the median frequency of the band filters 12 through 21. The integrating intervals for the integrators 32 through 41, which correspond to the impulse lengths of the impulse sequences A and C through F, are thus so determined in dependence upon the median transmissive frequencies of the band filters 12 through 21, so that the integrating intervals reduce at an increasing median transmission frequency of the band filters. The integration results are then transmitted from one of the integrators 32 through 41, responsive to closing of the corresponding switch, into the respective condenser 42 through 51 and stored in the latter.

The scanning installation 72 is controlled by the impulse sequence A which is produced through the impulse generator 73 and extends in synchronism with the impulse sequences of the generators 62 through 66 (FIG. 2). The installation is so constructed that it scans the integrating results at the outputs 86 through 95 at least one time for each shortest integration interval. Before the results reach the outputs 86 through 95, these are voltage-divided by means of the voltage dividers 98 through 107, so that the later described recording evidence a suitable gray tone scale for the spectral frequency distribution. For the band filters 9 and 10 with the frequency valve 0.5 to 2.5 and 2.5 to 4.5 the voltage division is 1 : 16, for the subsequent band filter pair 7, 8 it is 1 : 8, and so forth.

The output signals which are scanned at the outputs 86 through 95, by means of the scanning installation 72 are transmitted in sequence to the adjusting arrangement 80 of the recorder through the input 81, and a correspondingly speed-modulated recording is carried out through the recording jet 79 on the recording carrier 74.

Figure 3:
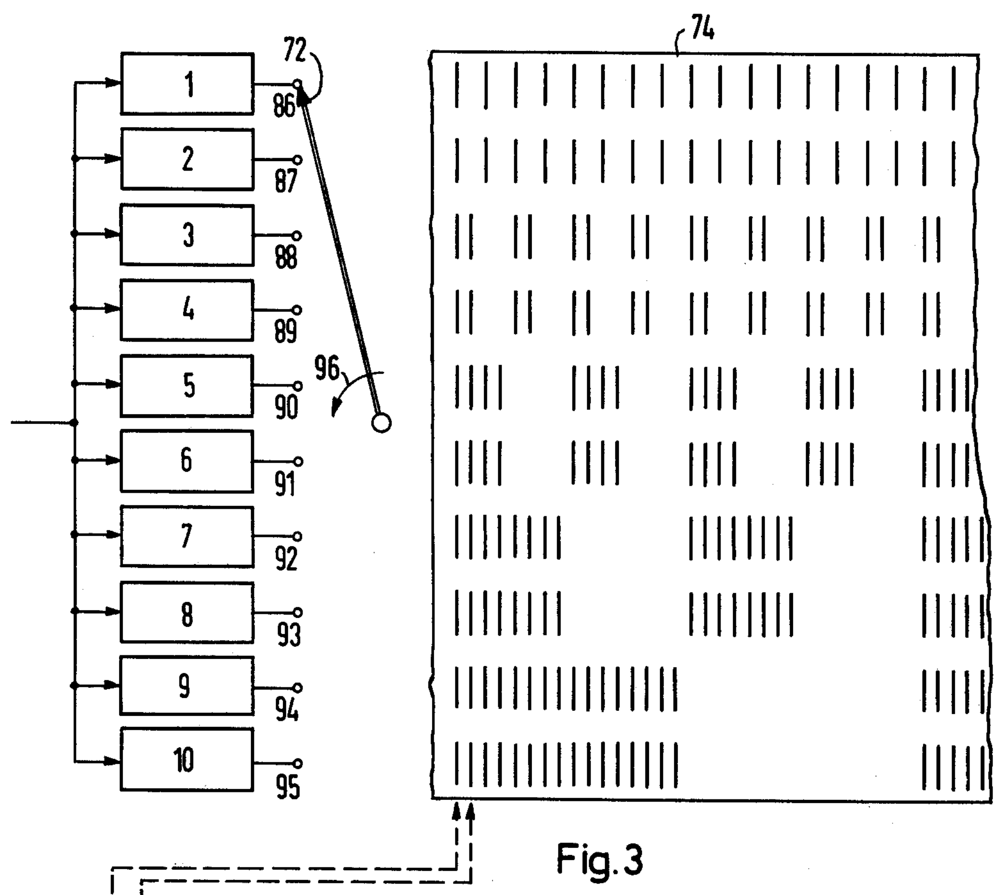
FIG. 3 is a recording made in an arrangement pursuant to FIG. 1.

An example for a recording of the signal which is to be analyzed is illustrated in FIG. 3. The jet recorder writes from above downwardly in synchronism with the scanning installation 72 (arrow 96) in rhythm with the scanning of the channel outputs 86 through 95 and intensity-modulates the recording corresponding to the voltages at the integrating condensers 42 through 51 with consideration to the dividing ratios of the voltage dividers 98 through 107, and in relationship to the present switched-in intervals of the switch elements 52 through 61, the latter of which are dependent upon the synchronously operating impulse sequences A, C through F of the synchronized impulse generators 62 through 66, 73. Obtained thereafter on the recording carrier 74 is a new integration information of the band filter channels 1 and 2 in conformance with each cycle of the scanning installation 72. In the illustrated example, there is alternatingly represented for the channels 1 and 2 a black- and a white-information, meaning, that the impulses of the impulse sequence A alternatingly correspond to a black- white-information. The integrated signals of the band filter channels 3 and 4 are then obtained two times after each other, and a new integrating information is then retrieved after each second cycle. The integrated signals of the channels 5 and 6 are obtained four times after each other and a new integrating information retrieved after each fourth cycle, and so forth. Consequently, on a small paper surface there is thus recorded a maximum of frequency information.

While there has been shown what is considered to be the preferred embodiment of the invention, it will be obvious that modifications may be made which come within the scope of the disclosure of the specification.

What is claimed is:

1. In a circuit arrangement for the frequency analysis of a signal, including a plurality of band filter channels having inputs to which the signal is transmitted in parallel connection, said channels including band filters of different boundary frequencies, rectifiers and integrators for integrating the rectified output signals of the band filters within predetermined integrating intervals; and a scanning installation being connected to the outputs of the latter for retrieving the integrating results after predetermined intervals, the improvement comprising: means comprising switch elements for determining the integrating intervals in dependence upon the median transmissive frequencies of said band filters so that the integrating intervals decrease with an increasing median transmissive frequency of said band filters; and switch elements having correlating means connected to the outputs of said integrators for correlating each integrating result to the corresponding integrating interval.

2. A circuit arrangement as claimed in claim 1, said integrating intervals being inversely proportional to the median transmissive frequencies of said band filters.

3. A circuit arrangement as claimed in claim 1, said scanning installation scanning said integrating results at least once for each shortest integrating interval; and a jet recorder being connected to said scanning installation, said jet recorder including a jet transmitter for directing a recording jet onto a recording carrier, means for producing a relative movement between the jet transmitter and the recording carrier in two approximately mutually perpendicular directions for effecting a linewise image recording, modulating means for modulating the intensity of the recorded lines and which is controlled by the output signal of said scanning installation, and means for synchronizing the scanning of the integrating results with the movement of the recording jet.

4. A circuit arrangement as claimed in claim 3, said jet transmitter transmitting a recording jet of constant strength onto said recording carrier for recording thereon, said modulating means comprising means for varying the relative speed between said jet transmitter and said recording carrier in at least one direction so as to effect a reduction in the speed for an intensity increase and an increase in speed for an intensity reduction.

5. In a circuit arrangement for the frequency analysis of a signal, including a plurality of band filter channels having inputs to which the signal is transmitted in parallel connection, said channels having band filters of different boundary frequencies, rectifiers and integrators for integrating the rectified output signals of the band filters within predetermined integrating intervals; and a scanning installation being connected to the outputs of the latter for retrieving the integrating results after predetermined intervals, means comprising switch elements for determining the integrating intervals in dependence upon the median transmissive frequencies of said band filters so that the integrating intervals decrease with an increasing median transmissive frequency of said band filters; said switch elements having voltage dividers connected to the outputs of said integrators for correlating the integrating results to the integrating intervals and whose dividing ratios correspond to the integrating intervals.

6. A circuit arrangement as claimed in claim 3, the dividing ratios of said voltage dividers being inversely proportional to the integrating intervals.

7. In a circuit arrangement for the frequency analysis of a signal, including a plurality of band filter channels having inputs to which the signal is transmitted in parallel connection, said channels including band filters of different boundary frequencies, rectifiers and integrators for integrating the rectified output signals of the band filters within predetermined integrating intervals; and a scanning installation being connected to the outputs of the latter for retrieving the integrating results after predetermined intervals; means comprising switch elements for determining the integrating intervals in dependence upon the median transmissive frequencies of said band filters so that the integrating intervals decrease with an increasing median transmissive frequency of said band filters; and said switch elements having correlating means connected to the outputs of said integrators for correlating each integrating result to the corresponding integrating interval; signal storage means connected to the outputs of said band filter channels, said signal storage means being connected to the integrators via the switch elements; and impulse generators delivering impulse sequences in which the duration of the impulses is equal to the current integrating interval.

8. A circuit arrangement as claimed in claim 7, said scanning installation comprising a stepping switch; and control means for effecting the stepwise connection of an output of said stepping switch to the channel outputs, said control means comprising an impulse generator operating in synchronism with said first-mentioned impulse generators.

* * * * *